United States Patent [19]
Ali

[11] Patent Number: 5,795,319
[45] Date of Patent: Aug. 18, 1998

[54] EASILY REMOVABLE URETERAL STENT

[75] Inventor: Mohammed Ali, Shorewood, Wis.

[73] Assignee: Circon Corporation, Racine, Wis.

[21] Appl. No.: 813,598

[22] Filed: Mar. 7, 1997

[51] Int. Cl.$^6$ ........................................... A61M 25/00
[52] U.S. Cl. ........................................................ 604/8
[58] Field of Search .................. 604/8, 9, 10, 281, 604/54, 280, 283, 284

[56] References Cited

U.S. PATENT DOCUMENTS

| | | | |
|---|---|---|---|
| 3,890,977 | 6/1975 | Wilson | 128/418 |
| 3,920,023 | 11/1975 | Dye et al. | 128/347 |
| 3,924,633 | 12/1975 | Cook et al. | 128/349 R |
| 3,938,529 | 2/1976 | Gibbons | 128/349 R |
| 3,995,642 | 12/1976 | Adair | 128/349 R |
| 4,117,836 | 10/1978 | Erikson | 128/2.05 R |
| 4,169,464 | 10/1979 | Obrez | 128/657 |
| 4,212,304 | 7/1980 | Finney | 128/349 R |
| 4,307,723 | 12/1981 | Finney | 128/349 R |
| 4,547,193 | 10/1985 | Rydell | 604/282 |
| 4,563,181 | 1/1986 | Wijayarathna et al. | 604/280 |
| 4,580,568 | 4/1986 | Gianturco | 128/345 |
| 4,610,657 | 9/1986 | Densow | 604/8 |
| 4,671,795 | 6/1987 | Mulchin | 604/281 |
| 4,713,049 | 12/1987 | Carter | 604/8 |
| 4,735,620 | 4/1988 | Ruiz | 604/281 |
| 4,787,884 | 11/1988 | Goldberg | 604/8 |
| 4,790,809 | 12/1988 | Kuntz | 604/8 |
| 4,790,810 | 12/1988 | Pugh, Jr. et al. | 604/8 |
| 4,800,882 | 1/1989 | Gianturco | 128/343 |
| 4,813,925 | 3/1989 | Anderson, Jr. et al. | 604/8 |
| 4,820,262 | 4/1989 | Finney | 604/8 |
| 4,874,360 | 10/1989 | Goldberg et al. | 604/8 |
| 4,907,336 | 3/1990 | Gianturco | 29/515 |
| 4,913,683 | 4/1990 | Gregory | 604/8 |
| 4,931,037 | 6/1990 | Wetterman | 604/8 |
| 4,950,227 | 8/1990 | Savin et al. | 604/8 |
| 4,950,228 | 8/1990 | Knapp, Jr. et al. | 604/8 |
| 4,957,479 | 9/1990 | Roemer | 604/8 |
| 4,961,731 | 10/1990 | Bodicky et al. | 604/264 |
| 4,963,129 | 10/1990 | Rusch | 604/8 |
| 4,990,133 | 2/1991 | Solazzo | 604/8 |
| 5,035,706 | 7/1991 | Giantureo et al. | 606/198 |
| 5,037,403 | 8/1991 | Garcia | 604/280 |
| 5,041,126 | 8/1991 | Gianturco | 606/195 |
| 5,052,998 | 10/1991 | Zimmon | 604/8 |
| 5,116,309 | 5/1992 | Coll | 604/8 |
| 5,141,502 | 8/1992 | Macaluso, Jr. | 604/281 |
| 5,163,928 | 11/1992 | Hobbs et al. | 604/281 |
| 5,176,625 | 1/1993 | Brisson | 604/8 |
| 5,176,626 | 1/1993 | Soehendra | 604/8 |
| 5,221,253 | 6/1993 | Coll | 604/8 |
| 5,282,784 | 2/1994 | Willard | 604/8 |
| 5,282,824 | 2/1994 | Gianturco | 606/198 |
| 5,295,954 | 3/1994 | Sachse | 604/8 |
| 5,314,444 | 5/1994 | Gianturco | 606/195 |
| 5,314,472 | 5/1994 | Fontaine | 623/12 |
| 5,322,501 | 6/1994 | Mahmud-Durrani | 604/8 |
| 5,346,467 | 9/1994 | Coll | 604/8 |
| 5,354,263 | 10/1994 | Coll | 604/8 |
| 5,364,340 | 11/1994 | Coll | 604/8 |
| 5,380,270 | 1/1995 | Ahmadzadeh | 604/9 |
| 5,387,235 | 2/1995 | Chuter | 623/1 |
| 5,399,165 | 3/1995 | Paul, Jr. | 604/95 |
| 5,401,257 | 3/1995 | Chevalier, Jr. et al. | 604/265 |
| 5,401,258 | 3/1995 | Voda | 604/281 |
| 5,407,435 | 4/1995 | Sachse | 604/170 |
| 5,439,446 | 8/1995 | Barry | 604/96 |
| 5,443,498 | 8/1995 | Fontaine | 623/1 |
| 5,456,713 | 10/1995 | Chuter | 623/1 |
| 5,478,349 | 12/1995 | Nicholas | 606/198 |
| 5,480,423 | 1/1996 | Ravenscroft et al. | 623/1 |
| 5,507,767 | 4/1996 | Maeda et al. | 606/198 |
| 5,507,771 | 4/1996 | Gianturco | 606/198 |
| 5,527,354 | 6/1996 | Fontaine et al. | 623/1 |

*Primary Examiner*—David Isabella
*Attorney, Agent, or Firm*—Banner & Witcoff, Ltd.

[57] ABSTRACT

A ureteral stent includes an elongated tubular member having proximal and distal ends. The proximal end is configured for placement in the bladder and the distal end has a shape of a helical curl including a flex portion which is the second turn of the loop of the helical curl. The flex portion of the loop of the helical curl is positioned at an angle to the body portion between 15–175 degrees to allow for safe removal of the distal end from the kidney.

13 Claims, 2 Drawing Sheets

EASILY REMOVABLE URETERAL STENT

BACKGROUND OF THE INVENTION

This invention relates to a ureteral stent and more particularly to a novel ureteral stent that resists migration when positioned in a patient and facilitates placement and safe removal of the stent from the kidney.

Ureteral stents are often used to maintain fluid drainage from the renal pelvis to the bladder when the ureter is obstructed or otherwise impaired. The ureteral stent is usually provided with drainage means such as a lumen for directing fluid from the renal pelvis to the bladder. U.S. Pat. No. 4,531,933 discloses openings provided along the stent for communication with the lumen to aide in drainage. Other conventional stents include longitudinal grooves on the outer wall that function as fluid drainage channels. However, if the openings or channels of the lumen become encrusted with residues from the fluid being drained then the drainage capability of stent is impaired.

The ureteral stent must have the ability to be placed and be easily removed from the kidney. The shape of the distal end of the stent primarily affects the placement and removal of the stent from the kidney. For example, a hook shaped or J shaped kidney curl can present a problem when it is desired to remove the stent. The distally extending end of the curl can engage the interior of the kidney, such as in the area of the renal pelvis. Other conventional stents have been provided that include a full circle or multiple curls. Often times the shape of the distal curl may cause the tip of the curl to catch the ureteropelvic junction. This can cause the stent to fold and kink in the ureter. Further, improper stent design can result in the stent being pulled into the ureter with the curl folded on itself.

U.S. Pat. Nos. 4,212,304 and 4,307,723 disclose ureteral stents having hooks at each end which are provided for preventing migration and expulsion. A ureteral stent having proximal and distal ends in the form of hooks and having open lumen at both ends is described in U.S. Pat. No. 4,610,657. U.S. Pat. No. 4,790,810 discloses a ureteral connector stent of adjustable length. The connector stent comprises an elongated straight tubular member and a connector provided for coupling the tubular member with a curled end. The curled end is generally in a helical shape with a distal tip curling less then a full 360°. U.S. Pat. No. 4,212,304 provides a ureteral stent having hooks at each end for preventing migration and expulsion. Helical ureteral stents are disclosed in U.S. Pat. Nos. 4,531,933 and 4,813,925 wherein the stents include a pigtail curl at the distal end which has a distal tip formed in a 360° curve and distal curls in excess of 360° ranging from approximately 1¼ turns to as many as 2 to 3 full turns.

While the conventional stents allegedly resist migration, provide adequate infusion and or drainage, there is a need for a stent which is completely safe in its insertion and removal from the kidney while providing superior drainage characteristics and resistance to migration.

SUMMARY OF THE INVENTION

A coiled stent is provided which is simple in construction and relatively easy to insert cystoscopically and is safe for use by the patient. Additionally, the novel design of the coiled stent provides effective means for preventing upward or downward migration of the stent yet provides a secure position when the patient is active. The design also provides safe, facile removal of the stent from the kidney.

It is an object of the present invention to provide a coiled stent which is relatively inexpensive, safe and efficient in use and which may be inserted utilizing conventional techniques.

Another object of the present invention is to provide a new ureteral stent having novel retention means on at least one end thereof.

It is another object of the present invention to provide a ureteral stent which includes a distal curl shaped to be received in the kidney and shaped to facilitate placement of the distal tip in the renal pelvis or calyx of choice.

A further object of the present invention is to provide a stent having a renal curl placed in an angle from about 0° to about 175° from the body portion of the stent to ensure easy and non-traumatic removal through the ureter, and particularly to prevent kinking of the stent upon removal.

Briefly, describing one aspect of the present invention, there is provided a ureteral stent comprising an elongated flexible tubular member having proximal and distal ends, the proximal end for placement in the bladder, the distal end including retention means for retaining the distal end in the kidney, the distal end retention means comprising the distal end being set in the shape of a helical curl having a flex portion which is clearly seen as the second turn of a loop of the helical curl in the same plane of the body portion when the angle measured between the body portion and the flex portion of the helical curl is 0°–10°, the novel improvement being the flex portion or second turn of the loop of the helical curl being positioned at an angle to the body portion being measured between 15° to 175° to allow for safe facile removal of the distal end from the kidney.

Further objects and advantages will become apparent from a consideration of the following drawings and detailed description.

DESCRIPTION OF THE PREFERRED EMBODIMENT

Figure 1:
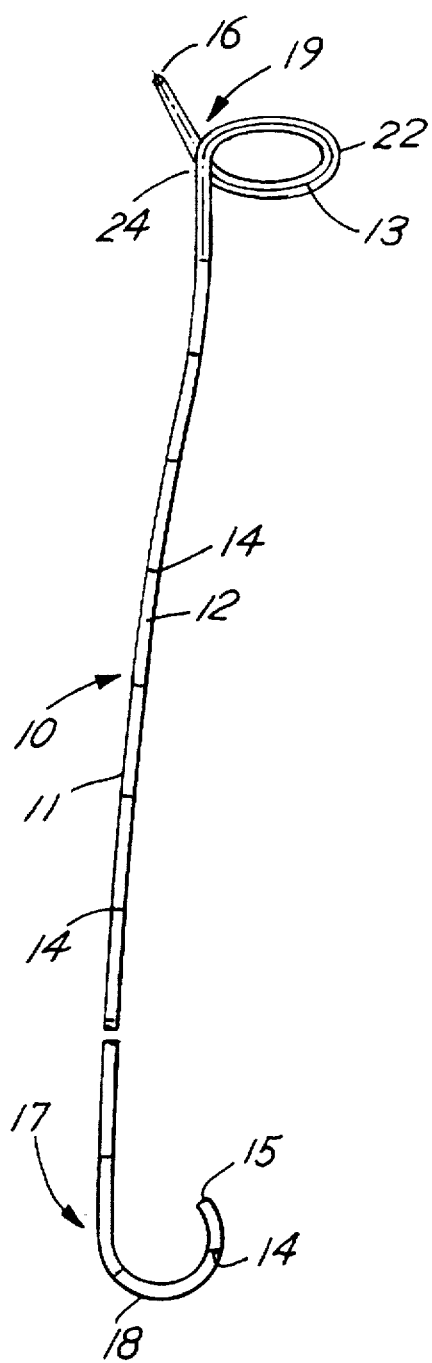
FIG. 1 is a front elevational view of a ureteral stent constructed in accordance with the present invention.

Reference will now be made to an embodiment illustrated in the drawings and specific language which will be used to describe the same. It will nevertheless be understood that no limitation of the scope of the invention is thereby intended, such alterations and further modifications in the illustrated device, as such further applications of the principles of the invention as illustrated therein as being contemplated as would normally occur to one skilled in the art to which the invention relates.

The invention provides a ureteral stent comprising an elongated tubular member having a generally straight body portion and opposed end portions with means for retaining the distal end in the kidney and optionally, means for retaining the proximal end in the bladder. The bladder end of the ureteral stent may have any of a variety of configurations providing a desired retaining effect or it may be entirely straight having no configuration for retention. The distal end portion of the invention has a particular configuration which advantageously serves several functions. The curve portion provides means for retaining the distal end in the kidney. The curl on the distal end is positioned to be angled from the body portion or elongated tubular member of the ureteral stent in such a way to facilitate placement and removal of the stent in a safe manner. The effect of the curl being positioned away from the body portion of the stent, desirably at angles ranging from 15° to 175° allows the curl to be partially uncoiled in the renal pelvis and for it to be removed without kinking or being pulled down intact into the ureteral.

A ureteral stent incorporating one embodiment of the invention is generally indicated by the reference No. 10 in FIG. 1. The stent comprises an elongated tubular member 11 of substantially uniformed diameter throughout its length. The tubular member may be formed from a variety of known materials which are biocompatible and have desired physical properties to be fabricated in the form hereafter described. An example of a suitable material is a silicon, thermoplastic material or elastomers or any material known to a skilled worker in the art, which combines the longitudinal rigidity necessary for extending difficult obstructions with the softness necessary for patient comfort.

The stent 10 includes a center body portion 12 which can be positioned within the ureteral. The body portion is preferably a substantially straight portion, but having sufficient flexibility to be passed into the ureteral. The stent includes a central lumen, not shown, communicating with several holes 14 along the length of the tubular member 11. The ureteral stent thereby provides fluid communication along its length from the distal end to the proximal end. The stent is formed from a radiopaque material to permit visualization by x-ray, and may include a center line 13 placed along the stent which may be viewed cystoscopically. The central lumen may extend fully to proximal tip 15 and distal tip 16 although it is not essential. When the stent is placed within the ureter with the proximal end in the usual fashion, further communication is provided by means of the central lumen and the holes 14 and when provided, end openings at the proximal and distal ends.

The stent includes a proximal end 17 which is provided with retention means for retaining the proximal end in the bladder, or alternatively, it may be free of retention means to serve as a drain. If retention means are utilized, they may assume a variety of forms such as those commonly used in the prior art. For example, the proximal end may include a J-shaped curve 18. Holes 14 are also provided in the proximal end portion of the stent.

Figure 17:
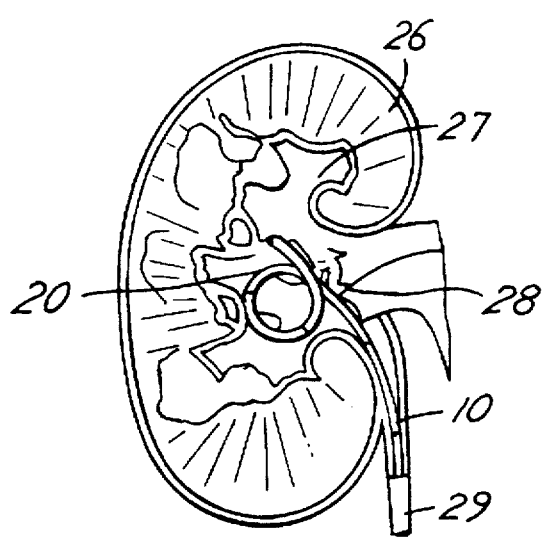
FIG. 17 is a cross sectional view of a kidney and ureter showing the distal end of the ureteral stent of FIG. 5 of the present invention.
Figure 2:
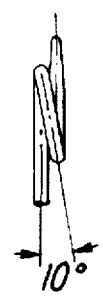
FIG. 2 is a left side view of a kidney curl of a ureteral stent found in the prior art, wherein the curl is positioned at 10° from the body portion of the stent.
Figure 3:
FIG. 3 is a left side view of the ureteral stent constructed in accordance with the present invention when the curl of the distal end is positioned 15° from the body portion of the stent.
Figure 4:
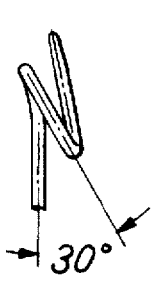
FIG. 4 is a left side view of the ureteral stent constructed in accordance with the present invention when the curl of the distal end is positioned 30° from the body portion of the stent.
Figure 5:
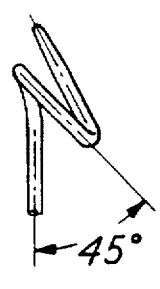
FIG. 5 is a left side view of the ureteral stent constructed in accordance with the present invention when the curl of the distal end is position 45° from the body portion of the stent.
Figure 6:
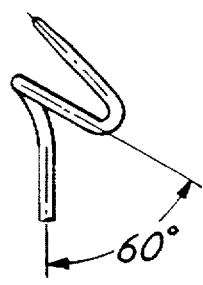
FIG. 6 is a left side view of the ureteral stent constructed in accordance with the present invention when the curl of the distal end is positioned 60° from the body portion of the stent.
Figure 7:
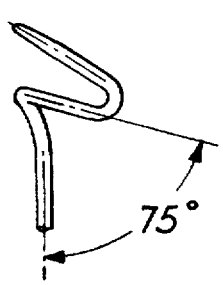
FIG. 7 is a left side view of the ureteral stent constructed in accordance with the present invention when the curl of the distal end is positioned 75° from the body portion of the stent.
Figure 8:
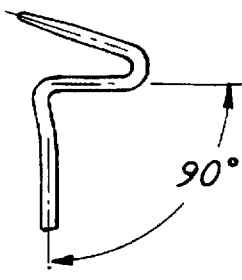
FIG. 8 is a left side view of the ureteral stent constructed in accordance with the present invention when the curl of the distal end is positioned 90° from the body portion of the stent.
Figure 9:
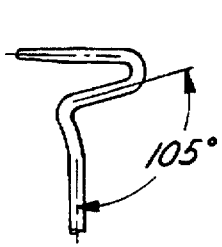
FIG. 9 is the left side view of the ureteral stent constructed in accordance with the present invention when the curl of the distal end is positioned 105° from the body portion of the stent.
Figure 10:
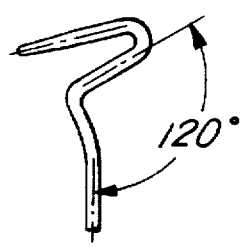
FIG. 10 is the left side view of the ureteral stent constructed in accordance with the present invention when the curl of the distal end is positioned 120° from the body portion of the stent.
Figure 11:
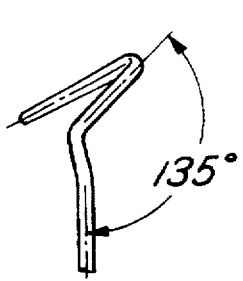
FIG. 11 is the left side view of the ureteral stent constructed in accordance with the present invention when the curl of the distal end is positioned 135° from the body portion of the stent.
Figure 12:
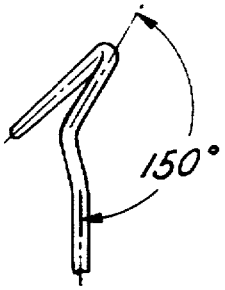
FIG. 12 is the left side view of the ureteral stent constructed in accordance with the present invention when the curl of the distal end is positioned 150° from the body portion of the stent.
Figure 13:
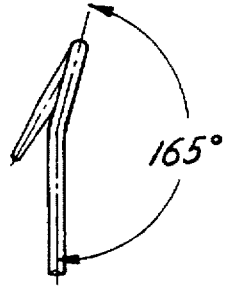
FIG. 13 is the left side view of the ureteral stent constructed in accordance with the present invention when the curl of the distal end is positioned 160° from the body portion of the stent.
Figure 14:
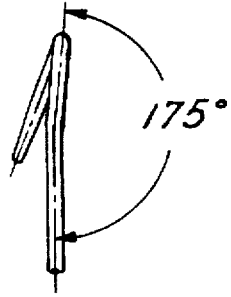
FIG. 14 is the left side view of the ureteral stent constructed in accordance with the present invention when the curl of the distal end is positioned 175° from the body portion of the stent.
Figure 15:
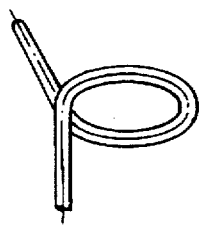
FIG. 15 is the front elevational view of the ureteral stent shown in FIG. 5 of the present invention.
Figure 16:
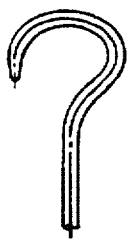
FIG. 16 is a front elevational view of the ureteral stent shown in FIG. 11 of the present invention.

The ureteral stent also includes a distal end 19 which includes retention means for retaining the distal end in the kidney. The distal end retention means comprises a distal end being set in the shape of a helical curl 20 with a flex portion 22. The flex portion 22 is viewed as a second turn in a helical curl from the body portion 12. The first turn 24 is where the helical curl meets the body portion 12 of the stent. The second turn is the flex portion 22 which follows the axis or plane of the body portion 12 of the stent 10 when the angle between the body portion and the flex portion is 0°–10° as shown in FIG. 2, which is a conventional distal end of a stent. The flex portion 22 and second turn may be extended from the body portion at angles ranging from 15° to 175° as shown in FIGS. 3 through 14 of the drawings. The moving of the flex portion 22 away from the body portion of the stent allows for facile removal of the stent from the kidney. At a placement of 90°, the flex portion 21 is perpendicular to the axis of body portion 12. The flex portion being positioned away from the body portion is similar to the distal end of a conventional stent being partially unfolded when being removed from the kidney. In this regard, when the distal end of the present invention is inserted into the kidney in a partially unfolded yet secure position it facilitates the safe removal of the stent from the kidney. The placement of the ureteral stent 10 in a kidney 26 is shown in FIG. 17. The distal end 19 is placed in the renal cavity 27 with the helical curl positioned away from the ureteropelvic junction. The holes 14 provide for fluid communication through the lumen of the stent down through the ureter to the bladder. The helical curl 20 retains the distal end of the stent in the kidney. The configuration of the distal end of the stent permits easy placement of the distal end in the renal pelvis.

FIGS. 2, 3–14 show various angles between the body portion 12 of the stent 10 and flex portion 22 which accommodate a partial or substantially complete unfolding or uncoiling of the helical curl 20 which provides for safe, easy stent removal. While in the renal cavity 27, the helical coil 20 fits comfortably within renal pelvis 28.

The stent 10 can be withdrawn simply by pulling the stent downwardly through the ureter 29. The curl, being angled from the body of the stent, is already offset or displaced to facilitate removal. Since the curl 20 is displaced, the distal end 19 is prevented from catching in the ureteropelvic junction. This also prevents the curl from being kinked or folded upon itself and being pulled down into the ureter without first uncoiling.

The presence of the second or flex portion 21 and its helical curl of the present invention being angled from the body portion 20, so that it is partially unfolded, and prevents the curl from being pulled into engagement with the ureteropelvic junction.

Once a physician has selected a stent 10 for use in the patient, after considering the normal size of the ureteral passage and the length of the ureter, the placement of the ureteral stent may by accomplished in accordance with known prior art techniques. A wire stylet, not shown, which can be formed of stainless steel, is inserted into the proximal end 17 of the stent 10, into the lumen.

The stent 10 is then drawn over the stylet to straighten the proximal end, and the curved distal end 19. The stylet is inserted up to, but not beyond, the distal end 19 and can be immobilized in the stent 10 by any suitable known locking means, not shown.

Confirmation that the renal pelvis 28 has been entered by the stent 10 can be obtained by x-ray. If desired, radiopaque measurement markings or other suitable radiopaque indicia can be incorporated on the stent 10 and is visible during x-ray examination to aid in confirming the position of the stent 10.

After the stent 10 has been inserted into a predetermined distance into the renal pelvis 28, the wire stylet is withdrawn, enabling the curls to form in the distal end 19 creating the helical curl 20. The helical curl bears against the walls of the renal pelvis 28 and ureter 29.

Alternatively, the ureteral stent 10 may be placed in the ureteral 29 during surgery.

Dimensions for the ureteral stent of the present invention are not critical, however, they include internal diameters of 4.5 to 8.5 French, and lengths ranging from 20 cm. to 32 cm. Drainage holes are preferably located about every 2 cm.

In view of the above, it will be seen that several objects of the present invention are achieved and other advantages results attained.

As various changes can be made in the above constructions and methods without departing from the scope of the invention, it is intended that all matter contained in the above description or shown in the accompanying drawings shall be interpreted as illustrated and not in a limiting sense.

What is claimed is:

1. A ureteral stent for maintaining drainage between the kidney and bladder comprising;

an elongated flexible tubular member having proximal and distal ends connected by a body portion having an axis including a central lumen and a plurality of holes to provide fluid communication between the proximal and distal ends, the proximal end for placement in the bladder, the distal end including retention means for retaining the distal end in the kidney, the distal end retention means comprising the distal end being set in the shape of helical curl, the helical curl having a flex portion which is viewed as the second turn of a loop of the helical curl in the same plane of the body portion when the angle measured between the body portion and the flex portion of the helical curl is 0°–10°, said flex portion of the helical curl being positioned at an angle to the body portion being measured between 15° to 175° to allow for safe and facile removal of the distal end from the kidney.

2. The ureteral stent of claim 1 in which the flex portion of the helical curl is placed at an angle of 30° from the body portion.

3. The ureteral stent of claim 1 in which the flex portion of the helical curl is placed at an angle of 45° from the body portion.

4. The ureteral stent of claim 1 in which the third portion of the helical curl is placed at an angle of 60° from the body portion.

5. The ureteral stent of claim 1 in which the flex portion of the helical curl is placed at an angle of 75° from the body portion.

6. The ureteral stent of claim 1 in which the flex portion of the helical curl is placed at an angle of 90° from the body portion.

7. The ureteral stent of claim 1 in which the flex portion of the helical curl is placed at an angle of 105° from the body portion.

8. The ureteral stent of claim 1 in which the flex portion of the helical curl is placed at an angle of 120° from the body portion.

9. The ureteral stent of claim 1 in which the flex portion of the helical curl is placed at an angle of 135° from the body portion.

10. The ureteral stent of claim 1 in which the flex portion of the helical curl is placed at an angle of 150° from the body portion.

11. The ureteral stent of claim 1 in which the flex portion of the helical curl is placed at an angle of 165° from the body portion.

12. The ureteral stent of claim 1 in which the flex portion of the helical curl is placed at an angle of 175° from the body portion.

13. The ureteral stent of claim 1 in which the proximal end has retention means for retaining the proximal end in the bladder.

* * * * *